United States Patent [19]

Konishi et al.

[11] Patent Number: 5,439,858
[45] Date of Patent: Aug. 8, 1995

[54] HYDRATED GRANULAR CARRIER PREPARED FROM POLYVINYL ALCOHOL AND ACTIVATED CHARCOAL FOR BIOLOGICAL TREATMENT APPARATUS

[75] Inventors: Kozo Konishi; Shoichi Chizaki, both of Ichihara; Shuzo Fujii; Yoshiyuki Takashima, both of Tokyo, all of Japan

[73] Assignee: Denka Consultant and Engineering Co., Ltd., Tokyo, Japan

[21] Appl. No.: 174,367

[22] Filed: Dec. 28, 1993

[30] Foreign Application Priority Data

Jun. 30, 1993 [JP] Japan ................. 5-186723

[51] Int. Cl.$^6$ ............ B01J 37/36; C12N 11/00; C12N 11/02; C12N 11/08
[52] U.S. Cl. ..................... 502/7; 435/174; 435/177; 435/180; 435/262.5
[58] Field of Search ............ 435/174, 177, 180, 262.5; 502/7

[56] References Cited

FOREIGN PATENT DOCUMENTS 269797 11/1987 Japan .
1-60318 12/1989 Japan .
2-21317 5/1990 Japan .
4-305295 10/1992 Japan .

Primary Examiner—David M. Naff
Attorney, Agent, or Firm—Fisher & Associates

[57] ABSTRACT

A hydrated granular carrier is prepared for microbe immobilization in a biological treatment apparatus such as for treating waste water and exhaust gas. The carrier contains hydrated granular gel particles coated with a finely ground organic powder. The gel particles are made of a polymer insoluble in cold water but soluble in hot water. In making the hydrated gel particles, heated water is added to the polymer while stirring at high speed. Then, the finely ground organic powder is added together with heated water while stirring at high speed to coat the finely ground organic powder on the gel particles. Preferably, the polymer is polyvinyl alcohol having a degree of polymerization of 1000 to 2500 and a degree of saponification of 98% or more. Heated water added to the polyvinyl alcohol is added by spraying at 10 to 15 liters per minute at a temperature of 40° to 100° C. in an amount of 50 to 150 parts by weight based on 100 parts by weight of the polyvinyl alcohol. The organic powder is activated charcoal having a particle size of 200 mesh or less in an amount of 3 parts by weight or more, and the water added with the charcoal is at 40 to 100° C. in an amount of 5 to 20 parts by weight. The high speed stirring is at 500 to 1000 rpm.

1 Claim, No Drawings

HYDRATED GRANULAR CARRIER PREPARED FROM POLYVINYL ALCOHOL AND ACTIVATED CHARCOAL FOR BIOLOGICAL TREATMENT APPARATUS

BACKGROUND OF THE INVENTION

This invention relates to a hydrated granular carrier for a biological treatment apparatus and a method for producing the same and, more particularly, to a living microbe immobilizing carrier used for a biological treatment apparatus for treating waste water and exhaust gas produced in both a living system and an industrial system and a method for producing the same.

A living microbe immobilizing carrier for a biological treatment apparatus which is currently put into practice is a granular carrier comprising completely saponified granular polyvinyl alcohol (PVA) particles and finely ground organic powder, such as finely ground activated charcoal powder coated on the granular particles, and is adapted to utilize adsorption characteristics of the finely ground organic powder coated on the granular particles. Such a conventional carrier is typically disclosed in each of Japanese Patent Publication No. 60318/1989 and Japanese Patent Publication No. 21317/1990. Immobilization of living microbes is carried out by immersing the carrier particles in an aqueous solution in which the living microbes are cultured. The carrier is used in the form of a packed bed or a fluidized bed in the biological treatment apparatus. When the carrier is used in the form of a packed bed, it is required to reduce volume change to a weight of the carrier which has water adsorbed thereto in a treatment apparatus; whereas when it is used in the form of a fluidized bed, it is required that the granular particles exhibit increased strength and the finely ground organic powder is coated on the granular particles with increased strength.

In order to efficiently immobilize the living microbes on a surface of the carrier, it is essential that the finely ground organic powder on a surface of the granular particles exhibits satisfactory adsorption properties and the granular particles exhibit satisfactory water absorption properties. Water absorption properties of the carrier depend on water retention of the polymer of which the granular particles for the carrier are formed and an internal structure of the granular particles. Also, durability of the carrier depends on the internal structure of the granular particles and coat strength of the finely ground organic powder on the granular particles. Nevertheless, the conventional carrier was not fully considered on a function of immobilizing living microbes thereon, durability of the carrier and the like.

SUMMARY OF THE INVENTION

The present invention has been made in view of the foregoing disadvantage of the prior art.

Accordingly, it is an object of the present invention to provide a hydrated granular carrier for a biological treatment apparatus which is capable of exhibiting a satisfactory living-microbe immobilizing function.

It is another object of the present invention to provide a hydrated granular carrier for a biological treatment apparatus which is capable of being decreased in volume change to load and exhibiting satisfactory durability.

It is a further object of the present invention to provide a hydrated granular carrier for a biological treatment apparatus which is capable of exhibiting increased mechanical strength.

It is still another object of the present invention to provide a method for producing a hydrated granular carrier which is capable of providing a hydrated granular carrier which is capable of provided a hydrated granular carrier which is decreased in volume change to load and exhibits satisfactory durability and increased mechanical strength.

DETAILED DESCRIPTION OF THE PREFERRED EMBODIMENT

In accordance with one aspect of the present invention, a hydrated granular carrier for a biological treatment apparatus is provided. The carrier comprises hydrated granular gel particles made of a polymer which is insoluble in cold water and soluble in hot water and finely ground organic powder coated on the hydrated granular gel particles in an amount of 3 parts by weight or more based on 100 parts by-weight of the hydrated granular gel particles, resulting in having a water content of about 30 to 60%.

In accordance with another aspect of the present invention, a method for producing a hydrated granular carrier for a biological treatment apparatus is provided. The method comprises the steps of adding water heated to 40 to 100° C. to polymer insoluble in cold water and soluble in hot water in an amount of 50 to 150 parts by weight based on 100 parts by weight of the polymer while stirring at a high speed, to there by prepare hydrated granular gel particles. Finely ground organic powder is then added in an amount of 3 parts by weight or more, together with the heated water in an amount of 5 to 20 parts by weight to the hydrated granular gel particles while stirring at a high speed to coat the finely ground organic powder on the granular particles.

The hydrated granular carrier of the present invention comprises hydrated granular gel particles made of a polymer which is insoluble in cold water and soluble in hot water and finely ground organic powder coated on the hydrated granular gel particles in an amount of 3 parts by weight or more based on 100 parts by weight of the hydrated granular gel particles, result in having a water content of about 30 to 60%.

In the present invention, powder of a hydrophilic polymer material, such as polyvinyl alcohol (PVA) or its derivatives, is used for the hydrated granular gel particles and powder of PVA, insoluble in cold water and soluble in hot water which has a saponification degree of about 95 mol % or more, is conveniently used for this purpose.

In general, in order that granular particles of polymer exhibit satisfactory water absorption properties, it is required that an internal structure of the particles has a suitable void and polymer particle elements, of which each of the granular particles is formed, are firmly and uniformly bonded together through a contact surface therebetween. The internal structure of the granular particles having such characteristics is obtained by instantaneously melting, from the beginning in a granulation step, a surface of the polymer particle elements through which the particle elements are contacted with each other to bond the particle elements together, to thereby coalesce the polymer particle elements together through the melted surface in order, resulting in preparing granular particles. In view of such a fact, the present invention is so constructed that water heated to a temperature of 40 to 100° C. is added to the polymer in an amount of 50 to 150 parts by weight based on 100 parts by weight of the polymer while stirring at an increased speed, to thereby prepare the above-described hydrated granular gel particles. Such construction of the present invention permits portions of the polymer particle elements contacted with each other to be bonded together in a gel-like manner and uniformly thoroughly from an interior of each of the granular particles to a surface thereof.

Then, the finely ground organic powder is added, together with 5 to 20 pans by weight of the heated water, to the thus-prepared granular gel particles while stirring at a high speed, resulting in providing the hydrated granular carrier which has a water content of about 30 to 60% and has 3% by weight or more of the finely ground organic powder attached thereto.

A water content of the carrier between 30% to 60% is desirable in that it ensures production of the hydrated granular gel particles and permits the organic powder to exhibit a function as a binder.

Significant or important factors in the method of the present invention which is constructed so as to instantaneously melt, from the beginning in the granulation step, the surface of the polymer particle elements through which the particle elements are contacted with each other to bond the particle elements together, to thereby coalesce the polymer particle elements together through the melted surface in order, resulting in forming the granular particles include a temperature of the heated water, the amount of addition thereof, a speed of addition thereof and a manner of addition thereof. A temperature required for instantaneously melting the contact surface of the polymer particle elements to bond the particle elements with each other through the melted contact surface is between 40° C. and 100° C. and preferably between 60° C. and 80° C. A decrease in temperature of the heated water to a level below the temperature range causes a failure in coalescence between the polymer particle elements. An upper limit of a temperature of the heated water for coalescing the polymer particle elements together is not specified. However, the temperature of 80° C. or more is not generally preferable, because it causes coalescence of the particle elements sufficient to form agglomerates of the particle elements which fail to pass through a sieve of a predetermined mesh size, to thereby deteriorate yield of the granular particles.

The heated water is preferably added by means of a spray because it permits the water to be uniformly spread on the polymer particle elements. Also, a speed of addition of the heated water which is suitable to instantaneously melt the surface of the polymer particle elements through which the particle elements are contacted with each other to bond the particle elements together, to thereby coalesce the polymer particle elements together through the melted surface in order is about 10 to 15 l/rain under stirring conditions at a speed as high as 500 to 1000 rpm. The amount of heated water below the range causes a failure in coalescence between the polymer particle elements to be increased, whereas the amount above the range described above causes excessive coalescence of the particle elements to a degree sufficient to form agglomerates of the particle elements which fail to pass through a sieve of a predetermined mesh size and thereby deteriorate yields of the granular particles. The total amount of heated water which permits the carrier product to have a water content of 30 to 60% is 55 to 170 parts by weight.

The finely ground organic powder added during the granulation exhibits a function of preventing blocking of the granular gel particles produced. The amount of addition of the finely ground organic powder below 3 parts by weight fails to permit the powder to be coated on a whole surface of the particles. This causes blocking of the granular gel particles, leading to a reduction in yields of the particles, whereas the amount above 30 parts by weight causes a decrease in contact surface of the powder with the hydrated granular gel particles, leading to peeling of the powder from the particles in use. A mechanism of adding the heated water to the granular gel particles while stirring, at a high speed, the gel particles to which the finely ground organic powder has been added, to thereby instantaneously melt contact surface between the granular particles and organic powder, leading to coalescence between the particles and the powder is substantially-the same as that of the abovedescribed coalescence between the polymer particle elements. Thus, factors such as a temperature of the heated water, the amount of addition thereof, a speed at which the heated water is added, the manner of addition thereof and the like can be set as described above, wherein the amount of addition of the heated water is 5 to 20 parts by weight based on the total amount of materials added.

As described above, in the conventional carrier, the polymer particle elements in each of the granular particles are not firmly bonded together, although the polymer particle elements in the surface portion of each of the granular particles are firmly bonded together, because production of the granular particles is carried out before completion of bonding between the polymer particle elements due to an increase in the period of time required for melting of the polymer particle elements and bonding therebetween. Also, the conventional carrier has another disadvantage in that the finely ground powder is added after the surface of the granular particles is hardened, resulting in failing to coat the powder in an amount of 3 % or more on the granular particles and provide sufficient coat strength.

Further, the conventional carrier fails to exhibit sufficient mechanical strength and is increased in volume change to load in use, because the polymer particle elements are uniformly melted to a degree sufficient to fail in gelation of the particle elements.

On the contrary, the present invention permits gelation to be uniformly carried out thoroughly from the interior of the particle elements forming each of the granular particles to the surface thereof and the polymer particle elements to be bonded together through the contact portion therebetween in a gel-like manner, resulting in the carrier of the present invention being significantly decreased in volume change to load and exhibiting satisfactory durability.

Also, the present invention permits the finely ground organic powder which affects adsorption properties of the carrier to be added together with the heated water in the coating step subsequent to the granulation, so that the powder may be added in an increased amount to the granular particles to increase coating strength of the powder and ensure durability of the carrier.

The invention will be understood more readily with reference to the following examples and comparative example, however, these examples are intended to illustrate the invention and are not to be construed to limit the scope of the invention.

EXAMPLE 1

A Henschel mixer was charged with 100 parts by weight of perfectly saponified PVA (degree of polymerization: 1000 to 2500, degree of saponification: 98 mol % or more) and then a jacket of the mixer was fed with hot water to keep the temperature in the mixer at about 70° C. Then, the PVA was sprayed with 90 pans by weight of water to a temperature of about 80° C. at a rate of 12 l/rain while stirring at a speed as high as 500 rpm, resulting in hydrated granular gel particles of PVA being prepared.

Subsequently, 18 parts by weight of finely ground activated charcoal having a particle size of 200 mesh or less was charged in the mixer and sprayed with 12 parts by weight of water heated to a temperature of 80° C. under the above-described conditions while stirring at a high speed, leading to preparation of a carrier coated with the finely ground activated charcoal. Thus, prepared hydrated granular gel carrier of 2 to 12 mm in particle diameter, coated with the finely ground activated charcoal was as high as 90% or more in yield and had a water content of 45 %. All of the carrier precipitated upon being immersed in cold water and peeling of the finely ground activated charcoal from the carrier was not substantially observed. Also, the carrier exhibited water absorption of 40 to 70% after being immersed in water for one day and volume change of 25 % or less under load of 100 $g/cm^2$.

EXAMPLE 2

The procedure described in Example 1 was substantially repeated except that a stirring speed of the mixer was set to be 500 rpm and 90 pans by weight of heated water was sprayed at a rate of 10 l/rain, resulting in preparing hydrated granular gel particles of PVA. Then, 30 parts by weight of finely ground activated charcoal having a particle size of 250 mesh or less was charged in the mixer and sprayed with 20 parts by weight of water heated to a temperature of 80° C. at the same rate as described above while stirring at a high speed, resulting in a carrier of 2 to 4 mm in particle diameter coated with the finely ground activated charcoal being prepared. The hydrated granular gel carrier prepared was as high as 88 % or more in yield and had a water content of 50%, resulting in exhibiting substantially the same performance as that obtained in Example 1.

COMPARATIVE EXAMPLE

The Henschel mixer was charged with 100 parts by weight of perfectly saponified PVA and then sprayed with 15 parts by weight of cold water in substantially the same manner as in the examples described above, while keeping a temperature in the mixer at 50 to 80° C. and stirring at a speed as high as 500 rpm, to thereby obtain hydrated granular particles of PVA. Then, finely ground activated charcoal of 200 mesh or less in particle size was gradually added in an amount of 3 parts by weight which is an upper limit of the addition to the mixer, to thereby cause the finely ground activated charcoal to be coated on the granular particles, leading to preparation of a hydrated granular carrier covered with the finely ground activated charcoal. This granulation procedure, when the amount of addition of the activated charcoal is above 3 parts by weight, causes peeling of the charcoal from the granular particles to be increased, to thereby fail to coat more charcoal on the particles.

Thus, prepared hydrated granular carrier of 2 to 12 nun in particle diameter was about 80% in yield. When the carrier was immersed in cold water, about half of the carrier floated; thus, more than one day was required to cause all the carrier to precipitate. Also, a considerable amount of finely ground activated charcoal was peeled from the granular particles. The carrier exhibited water absorption of 20 to 50% after immersion for one day and volume change of 40 to 50% under load of 100 $g/cm^2$.

While the invention has been described with a certain degree of particularity with reference to the examples, obvious modifications and variations are possible in light of the above teachings. It is therefore to be understood that within the scope of the appended claims, the invention may be practiced otherwise than as specifically described.

What is claimed is:

1. A method for producing a hydrated granular carrier for a biological treatment apparatus, comprising the steps of:

adding water heated at 40 to 100 degrees Centigrade to polyvinyl alcohol having a degree of polymerization of 1000 to 2500 and a degree of saponification of 98 % or more in an amount of 50 to 150 pans by weight based on 100 parts by weight of said polyvinyl alcohol, said water added via spraying at a rate of 10 to 15 liters per minute while stirring said polyvinyl alcohol with a stirrer at a speed of about 500 to 1000 rpm, to thereby prepare hydrated granular gel particles; and adding finely ground activated charcoal having a particle size of 200 mesh or less in an amount of 3 parts by weight or more together with water heated at 40 to 100 degrees Centigrade in an amount of 5 to 20 parts by weight to said hydrated granular gel particles while stirring said particles with a stirrer at a speed of about 500 to 1000 rpm.

* * * * *